United States Patent
Kataoka et al.

(10) Patent No.: US 9,278,075 B2
(45) Date of Patent: Mar. 8, 2016

(54) PARTICLE COMPOSITION AND PHARMACEUTICAL COMPOSITION USING PARTICLE COMPOSITION

(75) Inventors: Kazunori Kataoka, Tokyo (JP); Ronald James Christie, Tokyo (JP); Nobuhiro Nishiyama, Tokyo (JP); Kanjiro Miyata, Tokyo (JP); Shigeto Fukushima, Tokyo (JP); Yu Matsumoto, Tokyo (JP); Takahiro Nomoto, Tokyo (JP); Yasuki Kato, Kashiwa (JP)

(73) Assignees: NANOCARRIER CO., LTD., Kashiwa-shi (JP); THE UNIVERSITY OF TOKYO, Tokyo (JP)

(*) Notice: Subject to any disclaimer, the term of this patent is extended or adjusted under 35 U.S.C. 154(b) by 204 days.

(21) Appl. No.: 13/979,546

(22) PCT Filed: Jan. 16, 2012

(86) PCT No.: PCT/JP2012/050683
§ 371 (c)(1),
(2), (4) Date: Sep. 23, 2013

(87) PCT Pub. No.: WO2012/096399
PCT Pub. Date: Jul. 19, 2012

(65) Prior Publication Data
US 2014/0017328 A1  Jan. 16, 2014

(30) Foreign Application Priority Data
Jan. 14, 2011  (JP) ................................. 2011-006318

(51) Int. Cl.
A61K 9/50 (2006.01)
A61K 38/19 (2006.01)
A61K 31/713 (2006.01)
A61K 31/711 (2006.01)
A61K 9/107 (2006.01)
A61K 47/48 (2006.01)

(52) U.S. Cl.
CPC ............... *A61K 9/5031* (2013.01); *A61K 9/107* (2013.01); *A61K 31/711* (2013.01); *A61K 31/713* (2013.01); *A61K 38/193* (2013.01); *A61K 47/48215* (2013.01); *A61K 47/48323* (2013.01)

(58) Field of Classification Search
None
See application file for complete search history.

(56) References Cited

U.S. PATENT DOCUMENTS

| 7,829,657 | B2 | 11/2010 | Kataoka et al. |
| 8,153,110 | B2 | 4/2012 | Kataoka et al. |
| 2008/0249049 | A1 | 10/2008 | Kataoka et al. |
| 2009/0258416 | A1 | 10/2009 | Kataoka et al. |
| 2010/0121043 | A1 | 5/2010 | Kataoka et al. |

FOREIGN PATENT DOCUMENTS

| WO | 99/61512 A1 | 12/1999 |
| WO | 2006/085664 A1 | 8/2006 |
| WO | 2007/099660 A1 | 9/2007 |
| WO | 2008/062909 | 5/2008 |

OTHER PUBLICATIONS

Matsumoto, Satoru; et. al. "Environment-Responsive Block Copolymer Micelles with a Disulfide Cross-Linked Core for Enhanced siRNA Delivery" Biomacromolecules, 2009, v.10, pp. 119-127.*
Singh, Rajeeva; et al. "Formation of N-substituted 2-iminothiolanes when amino groups in proteins and peptides are modified by 2-iminothiolane" Analytical Biochemistry, 1996, v. 236, 114-125.*
English translation of International Search Report for parent PCT application No. PCT/JP2012/050683.
English translation of International Preliminary Report on Patentability for parent PCT application No. PCT/JP2012/050683.
K. Miyata et al., J. Am. Chem. Soc. 2004, 126, 2355-2361.
K. Miyata et al., J. Am. Chem. Soc. 2008, 130, 16287-16294.
Extended European Search Report dated Dec. 8, 2014 for counterpart EP application No. 12733905.9, including European Search Opinion, Supplementary European Search Report and examined claims 1-6.
R. James Christie et al: "Effect of Polymer Structure on Micelles Formed between siRNA and Cationic Block Copolymer Comprising Thiols and Amidines", Biomacromolecules, vol. 12, No. 9, Aug. 24, 2011, pp. 3174-3185, ISSN: 1525-7797.
Satoru Matsumoto et al: "Environment-Responsive Block Copolymer Micelles with a Disulfide Cross-Linked Core for Enhanced siRNA Delivery", Biomacromolecules, vol. 10, No. 1, Jan. 12, 2009, pp. 119-127, ISSN: 1525-7797.

* cited by examiner

*Primary Examiner* — Mina Haghighatian
*Assistant Examiner* — Erin Hirt
(74) *Attorney, Agent, or Firm* — J-Tek Law PLLC; Jeffrey D. Tekanic; Scott T. Wakeman

(57) ABSTRACT

A composition of matter for use in encapsulating a drug is expressed by formula (1) or formula (2):

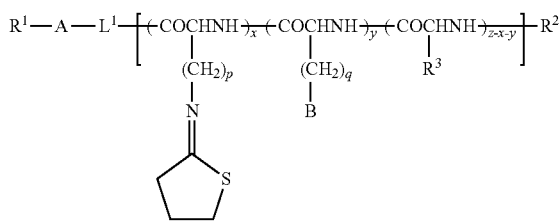

(1)

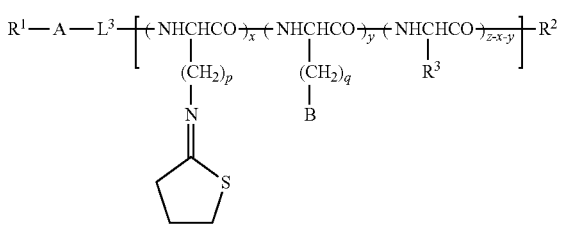

(2)

wherein $R^1$ and $R^2$ are each independently a hydrogen atom or a substituted or unsubstituted, linear or branched alkyl group having 1 to 12 carbon atoms; A is a hydrophilic polymer chain; $L^1$ and $L^3$ are each a linking group; B is a cation-containing group; $R^3$ is a side chain of an amino acid; z is an integer of 5 to 500; x is an integer of 40% or more of z; y is 0 or a positive integer; z-x-y is 0 or a positive integer; p is an integer of 1 to 10; and q is an integer of 1 to 10.

18 Claims, 6 Drawing Sheets

PARTICLE COMPOSITION AND PHARMACEUTICAL COMPOSITION USING PARTICLE COMPOSITION

CROSS-REFERENCE

This application is the US national stage of International Patent Application No. PCT/JP2012/050683 filed on Jan. 16, 2012, which claims priority to Japanese Patent Application No. 2011-006318 filed on Jan. 14, 2011.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
| --- | --- | --- |
| NCC004_seq_list.txt | Sep. 1, 2013 | 2.32 |

TECHNICAL FIELD

The present invention relates to a particle composition and to a pharmaceutical composition using the particle composition.

BACKGROUND ART

The application of siRNA to medical treatments is increasingly expected because siRNA can knock down target mRNA specifically and effectively. However, the development of an effective delivery system is indispensable to applying siRNA to medical treatments. In recent years, it has been clarified in clinical trials that the therapeutic effect on age-related macular degeneration (CNV) by intraocular administration of naked siRNA does not result from a sequence-specific gene knockdown effect mediated by siRNA, but rather results from a non-sequence-specific effect via recognition by the cell surface Toll-like receptor-3 (TLR-3); thus, the development of a carrier, which is stable outside of cells and is capable of accurately delivering siRNA into the cells in any in vivo application of siRNA, is considered to be important.

Thus far, a variety of cationic polymers have been provided as carriers for forming a polyion complex (PIC) with DNA and for introducing and expressing the nucleic acid into eukaryotic cells. For example, it is known that a poly(L-lysine) derivative in which a hydrophilic group (e.g., polyethylene glycol) and a hydrophobic group (e.g., a palmitoyl group) have been introduced via an ε-amino group of poly(L-lysine) forms a vesicle in the presence of cholesterol in an aqueous medium, and the vesicle aggregates gene-containing plasmid DNA to form a stable complex (Patent Literature 1). Further, a PIC formed of plasmid DNA with a copolymer derivative whose cation charge and disulfide cross-link density have been adjusted by the thiolation of an ε-amino group of poly (L-lysine) in a poly (L-lysine)-poly (ethylene glycol) copolymer is known to show high stability in an extracellular medium and to effectively release the DNA in an intracellular compartment (Non Patent Literature 1). Further, it has been confirmed that, when poly(N—[N-(2-aminoethyl)-2-aminoethyl]aspartamide (pAsp (DET))) having an ethylenediamine structure in a side chain and a block copolymer including the pAsp (DET) as one block component of the block copolymer are produced, such polymers exhibit low cytotoxicity and introduce plasmid DNA into cells with high efficiency to efficiently express a gene incorporated into the DNA (see Non Patent Literature 2, Patent Literature 2, and Patent Literature 3).

As described above, although a carrier effective for a high molecular weight nucleic acid such as DNA has been developed, a carrier capable of also forming a stable complex such as a PIC with a low molecular weight nucleic acid such as siRNA under physiological conditions and capable of suitably releasing the low molecular weight nucleic acid in cells has not been provided yet.

CITATION LIST

Patent Literature

[Patent Literature 1] WO 99/61512 A1
[Patent Literature 2] WO 2006/085664 A1
[Patent Literature 3] WO 2007/099660 A1

Non Patent Literature

[Non Patent Literature 1] K. Miyata et al., J. Am. Chem. Soc. 2004, 126, 2355-2361
[Non Patent Literature 2] K. Miyata et al., J. Am. Chem. Soc. 2008, 130, 16287-16294

SUMMARY OF THE INVENTION

In one aspect of the present teachings, a drug carrier is capable of forming a stable complex with a nucleic acid under physiological conditions and releasing the nucleic acid in cells.

In another aspect of the present teachings, a particle composition is comprised of a block copolymer and includes a drug carrier represented by formula (1) or formula (2) as the block copolymer:

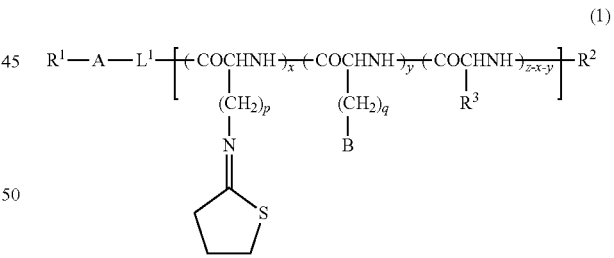

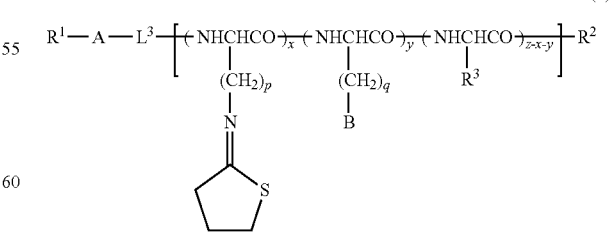

where:
$R^1$ and $R^2$ each independently represent a hydrogen atom or a linear or branched alkyl group having 1 to 12 carbon atoms which may have a substituent;

A represents a hydrophilic polymer chain;
L¹ and L³ each represent a linking group;
B represents a cation-containing group;
R³ represents a side chain of any amino acid;
z represents an integer of 5 to 500;
x represents an integer of 40% or more of z;
y represents an integer and may represent 0;
z-x-y represents an integer and may represent 0;
p represents an integer of 1 to 10; and
q represents an integer of 1 to 10.

According to another aspect of the present teachings, a pharmaceutical composition is provided. The pharmaceutical composition includes the particle composition and a drug encapsulated in the particle composition.

According to the present invention, it is possible to provide a carrier that is capable of forming a stable complex (pharmaceutical composition) with a nucleic acid and releasing the nucleic acid in cells. The carrier can be utilized as a drug carrier for a biopolymer such as a nucleic acid or a protein.

MODES FOR CARRYING OUT THE INVENTION

Figure 1:
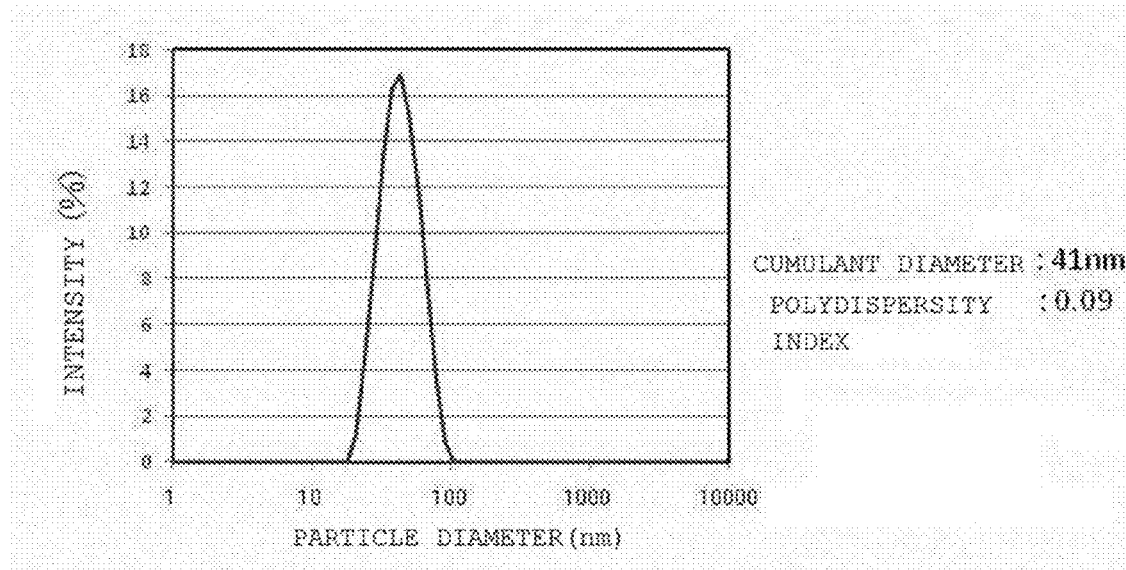
FIG. 1 is a histogram of the particle diameter distribution of a complex according to the present invention.

Preferred embodiments of the present invention are described below. However, the present invention is not limited to these embodiments. It should be noted that a particle composition comprised of a block copolymer and a pharmaceutical composition comprised of the particle composition and a drug (e.g., a biopolymer) encapsulated in the particle composition differ from each other in shape in some cases, but the compositions are both regarded as particles in this description.

A. Particle Composition

The particle composition of the present invention is comprised of a block copolymer, and includes a drug carrier as the block copolymer.

A-1. Drug Carrier

The drug carrier constituting the particle composition of one aspect of the present teachings is a block copolymer that includes a hydrophilic polymer chain segment and a polyamino acid-derived segment, and is represented by the following formula (1) or (2):

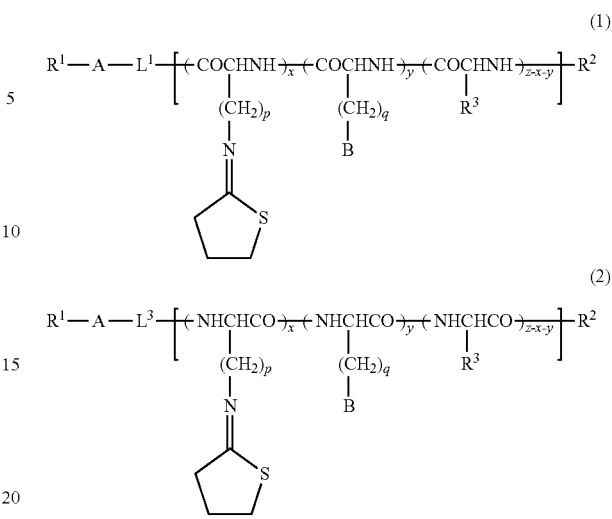

where: R¹ and R² each independently represent a hydrogen atom or a linear or branched alkyl group having 1 to 12 carbon atoms which may have a substituent; A represents a hydrophilic polymer chain; L¹ and L³ each represent a linking group; B represents a cation-containing group; R³ represents a side chain of any amino acid; z represents an integer of 5 to 500; x represents an integer of 40% or more of z; y represents an integer and may represent 0; z-x-y represents an integer and may represent 0; p represents an integer of 1 to 10; and q represents an integer of 1 to 10.

A represents a hydrophilic polymer chain that constitutes the hydrophilic polymer chain segment of the drug carrier. Any appropriate hydrophilic polymer may be employed as the hydrophilic polymer that constitutes the hydrophilic polymer chain. Examples of the hydrophilic polymer include poly(ethylene glycol), polysaccharide, poly(vinylpyrrolidone), poly(vinyl alcohol), poly(acrylamide), poly(acrylic acid), poly(methacrylamide), poly(methacrylic acid), poly(methacrylic acidester), poly(acrylic acid ester), polyamino acid, poly(malic acid), and derivatives thereof. Specific examples of the polysaccharide include starch, dextran, fructan, and galactan. Of those, poly(ethylene glycol) may be preferably used because terminal-reactive polyethylene glycols having a variety of functional groups at their terminus are commercially available, and polyethylene glycols having a variety of molecular weights are commercially available and are readily available.

The repetition number of the hydrophilic polymer in the hydrophilic polymer chain is preferably an integer of 30 to 20,000, more preferably an integer of 40 to 2,000, still more preferably an integer of 50 to 1,000.

The structure expressed in the brackets [ ] in each of formulas (1) and (2) is a structure that corresponds to the polyamino acid-derived segment (hereinafter referred to as (the) polyamino acid segment). The polyamino acid segment includes amino acid residues having a particular cyclic structure (hereinafter referred to as the amino acid segment having the cyclic structures) and (an) amino acid residue(s) having a (the) cation-containing group(s) (hereinafter referred to as the amino acid segment having a (the) cation-containing group(s)). A stable complex can be formed by virtue of the incorporation of those structures. The polyamino acid segment may include (an) amino acid residue (s) other than the amino acid segment having the cyclic structures and the amino acid segment having a (the) cation-containing group(s). The bonding order of the amino acid residues in the polyamino acid segment is arbitrary, and it may be a random structure or a block structure.

z represents the total number of units in the polyamino acid segment of the drug carrier. z represents an integer in the range of 5 to 500, the lower limit of the range may be 10, or also 20, and the upper limit of the range may be 200, or also 100.

The polyamino acid segment is a polypeptide in which any amino acids are bonded to each other by peptide bonds. Any amino acids may be used as the amino acids constituting the polypeptide, and specifically, lysine, ornithine, arginine, histidine, serine, aspartic acid, and glutamic acid can be suitably used. For example, by utilizing serine, aspartic acid, or glutamic acid as the amino acid (s), a predetermined cyclic structure can be introduced with high certainty.

x represents the number of amino acids having the cyclic structures. The percentage of the amino acids having the cyclic structures (corresponding to the cyclic structure content in the below-described Examples) is 40% or more of the total number of units in the polyamino acid segment in the drug carrier. That is, x represents an integer of 40% or more of z. When the percentage of the amino acids having the cyclic structures is 40% or more of the polyamino acid segment, a highly-stable micelle is easily obtained owing to increased hydrophobicity of the block copolymer and, as will be described below, intracellular endosomal escape easily occurs. Preferably, the percentage of the amino acids having the cyclic structures is 50% or more of the polyamino acid segment, and is more preferably 60% or more, still more preferably 70% or more, particularly preferably 85% or more of the polyamino acid segment. The percentage of the amino acids having the cyclic structures may be 100% of the polyamino acid segment. However, the percentage is preferably less than 100% and may be, for example, 95% or less in order to improve the ability to form a complex with a drug (e.g., a biopolymer) in a relatively easy manner (e.g., under physiological conditions) by utilizing the effect (properties) of the amino acids having the below-described cation-containing group(s). The amino acids having the cyclic structures are known to have the property of generating a positive charge in a low-pH environment such as in the endosome (e.g., the pH in the endosome is 5.5). It is also believed that this positive charge acts on the endosomal membrane, resulting in endosomal escape. The endosomal escape allows the complex to be completely taken up into an intracellular matrix in order to release an encapsulated drug into the nucleus. In addition, such amino acids having the cyclic structures do not generate a positive charge under physiological conditions, i.e., in a neutral-pH environment, and hence can be present in blood in a non-toxic state.

B represents the cation-containing group in the amino acid segment having the cation-containing group(s). The cation-containing group is any appropriate group containing a cation; for example, a group containing an ammonium cation can be given as an example thereof. By virtue of the incorporation of the amino acid segment having the cation-containing group(s), under physiological conditions the drug carrier can form a complex (e.g., a PIC) with a biopolymer (e.g., siRNA) to be used as the drug. Specifically, amidine groups, groups derived from diethylenetriamine, and groups selected from the group consisting the following formulae (i) to (iv) can be given as examples.

  (i);

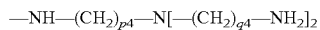  (ii);

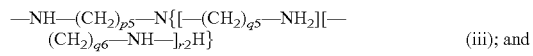  (iii); and

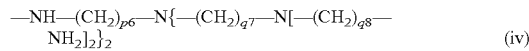  (iv)

Preferably, the group represented by formula (i) is used. Preferably, p3 to p6 and q3 to q8 each independently represent 2 or 3, more preferably 2. On the other hand, preferably r1 and r2 each independently represent an integer of 1 to 3.

The amino acid segment having the cation-containing group(s) may have a thiol group (—SH group) at the terminal of its side chain, i.e. the terminus of the cation-containing group. By reacting with each other, the thiol groups can to form a cross-link via a disulfide bond. This increases the association properties of the block copolymers with one another, resulting in a block copolymer that is capable of forming a micelle having high stability. Further, the disulfide bond is a bond that is easily cleaved in a reductive environment. Thus, a stable micelle can be maintained in a non-reductive environment, i.e., outside of cells, and an encapsulated product can be efficiently released in a reductive environment, i.e., inside of cells.

Thus, in one embodiment, B represents —NH$^+$=C(—NH)—(CH$_2$)$_q$—SH, and q represents an integer of 1 to 10, preferably an integer of 2 to 4.

y represents the number of amino acids having the cation-containing group(s). y represents an integer and may represent 0. y may represent, for example, an integer of 1 or more, an integer of 2 or more, or further, an integer of 5 or more. Further, y may represent, for example, an integer of 200 or less, an integer of 100 or less, an integer of 80 or less, an integer of 40 or less, or further, an integer of 20 or less.

Preferably, the percentage of the amino acid segment having the cyclic structures plus the amino acid segment having the cation-containing group(s) in the polyamino acid segment is 95% or more of the polyamino acid segment. That is, x+y preferably represents an integer of 95% or more of z. It should be noted that the polyamino acid segment in the block copolymer may be comprised of only the amino acid segment having the cyclic structures and the amino acid segment having the cation-containing group(s).

The ratio of the amino acid segment having the cyclic structures to the amino acid segment having the cation-containing group(s) in the polyamino acid segment need be appropriately set only in accordance with the application of the complex using the particle composition of the present invention and the drug(s) to be encapsulated. The ratio of the amino acid segment having the cyclic structure(s) and the amino acid segment having the cation-containing group(s) may be adjusted, for example, by appropriate setting involving adjusting the pH of the solvent to be used in the synthesis process for the block copolymer and/or using any appropriate catalyst. Specifically, the cyclic structure can be introduced with high certainty by using a high-purity catalyst (e.g., diisopropylethylamine) under an argon atmosphere and/or by setting the pH during dialysis in a purification process to a relatively high one (e.g., pH 6).

$R^3$ represents a side chain of any amino acid constituting the polyamino acid segment. Thus, the polyamino acid segment may include (an) amino acid-derived segment(s) (hereinafter also referred to as other amino acid segment(s)) constituting the polyamino acid segment other than the amino acid segment having the cyclic structures and the amino acid segment having the cation-containing group(s). For example, $R^3$ may represent a side chain of at least one kind of amino acid selected from the group consisting of lysine, ornithine, arginine, histidine, serine, aspartic acid, and glutamic acid.

The number of the other amino acid segments is not particularly limited, and the other amino acid segments are moieties other than the amino acid segment having the cyclic structures and the amino acid segment having the cation-containing group (s). For example, when the polyamino acid segment is comprised of (an) amino acid (s) having a basic side chain, the other amino acid segment (s) can function as cationic groups. The other amino acid segment (s) may be omitted.

With respect to the linear or branched alkyl group having 1 to 12 carbon atoms, among the groups represented by $R^1$ and $R^2$, a methyl group, an ethyl group, an n-propyl group, an isopropyl group, an n-butyl group, an sec-butyl group, a tert-butyl group, an n-pentyl group, an n-hexyl group, a decyl group, and an undecyl group can be given as examples.

As a substituent for the alkyl group, for example, an acetal-formyl group, a cyano group, a formyl group, a carboxyl group, an amino group, an alkoxycarbonyl group having 1 to 6 carbon atoms, an acylamide group having 2 to 7 carbon atoms, a siloxy group, a silylamino group, and a trialkylsiloxy group (alkylsiloxy groups are independent of each other and each have 1 to 6 carbon atoms) are given as examples. When the substituent, in particular the substituent in $R^1$, is a formyl group, a carboxyl group, or an amino group, it is possible to bind via such substituent any ligand, for example, an antibody or a fragment thereof, or another protein having functionality or targeting properties.

$L^1$ and $L^3$ are linking groups and represent a linking moiety between the hydrophilic polymer chain segment and the segment consisting of polyamino acids of the drug carrier. Specifically, the linking group represented by $L^1$ may be a linking group selected from —NH—, —O—, —O-$L^2$-NH—, —CO—, —CH$_2$—, and —O-$L^2$-S-$L^2$-NH— (where $L^2$'s each independently represent a $C_1$ to $C_6$ alkylene group), and $L^3$ may represent a linking group selected from —OCO-$L^4$-CO— and —NHCO-$L^4$-CO— (provided that $L^4$ represents a $C_1$ to $C_6$ alkylene group).

p and q each represent a repeating unit of a methylene group in a side chain moiety of the polyamino acid segment. p represents an integer of 1 to 10, preferably 3 or 4. q represents an integer of 1 to 10, preferably 3 or 4.

The block copolymer may be prepared, for example, by: (i) sequentially polymerizing a predetermined monomer with a hydrophilic polymer, and as necessary, performing substitution or conversion so that the side chains include the cyclic structures or cation-containing group(s); (ii) binding a polyamino acid constituting a polyamino acid segment moiety, which was polymerized in advance, to a hydrophilic polymer, and then as necessary, performing substitution or conversion so that the side chains of the polyamino acid include the cyclic structure or cation-containing group(s); or (iii) preparing a polyamino acid having the cyclic structures and the cation-containing(s) group in its side chains in advance, and then binding the polyamino acid to a hydrophilic polymer.

B. Particle Composition Further Including a Drug Carrier Having a Target Binding Site, or a Target Binding Carrier Having a Hydrophilic Polymer Chain, a Hydrophobic Polymer Chain, and a Target Binding Site Bound to a Hydrophilic Polymer Chain In one preferred embodiment, the particle composition of the present invention has a target binding site bound to a hydrophilic polymer chain terminus of the drug carrier. Further, in another preferred embodiment, the particle composition of the present invention further includes, as a block copolymer constituting the particle composition, a target binding carrier having a hydrophilic polymer chain, a hydrophobic polymer chain, and a target binding site bound to the hydrophilic polymer chain, in addition to the drug carrier. In these embodiments, the particle composition has a target binding site on its particle surface, and the drug carrier is bound to a drug (e.g., a biopolymer) to be encapsulated in the particle composition. The bond between the biopolymer and the drug carrier may be, for example, an ionic bond between the biopolymer and the cation-containing group, or a chemical bond such as a disulfide bond. The target binding site as used herein refers to a site having a biological recognition function, which is capable of specifically binding to a substance derived from a living organism and a virus to form a biological binding pair with the substance.

B-1. Drug Carrier Having a Target Binding Site

A drug carrier having a target binding site has a target binding site bound via any linking group to the terminus of the hydrophilic polymer chain segment side of the drug carrier. The use of the drug carrier having a target binding site can improve drug delivery to a desired target site. The target binding site may be formed, for example, by binding a compound having a target binding site to the terminus of the hydrophilic polymer chain side of the drug carrier. The compound having a target binding site may be any compound depending on the target tissue and purpose; for example, physiologically active substances such as an antibody or a fragment thereof, or another protein having functionality or targeting properties, a peptide, an aptamer, a sugar such as lactose, and folic acid can be given as examples thereof. When the drug carrier having a target binding site is used as a polymer unit having a target binding site, the drug carrier may be bound to a drug.

Specifically, the drug carrier having a target binding site may be represented, for example, by the following formula (3) or (4):

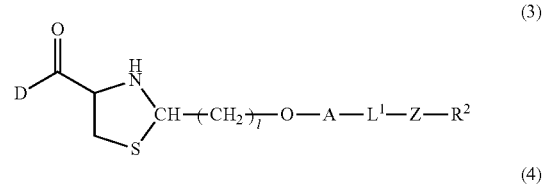

(3)

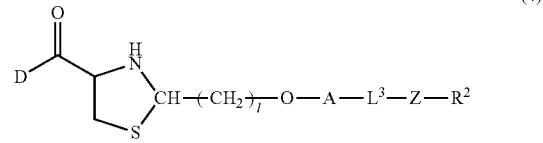

(4)

(in formulas: A, $R^2$, $L^1$, and $L^3$ are the same as those in formulas (1) and (2); Z represents any polyamino acid segment encompassed by formulas (1) and (2); l represents an integer of 1 to 5; and D represents a target binding site).

The target binding site (D in formulas (3) and (4)) of the drug carrier is preferably a peptide having a weight average molecular weight of 50 to 20,000, more preferably a peptide having a weight average molecular weight of 100 to 10,000, still more preferably a peptide having a weight average molecular weight of 150 to 3,000.

Further, D preferably represents a peptide having 1 to 200 amino acid residues, more preferably a peptide having 1 to 100 amino acid residues, still more preferably a peptide having 1 to 30 amino acid residues.

Peptides capable of specifically binding to integrin, which is involved in angiogenesis, intimal thickening, and malignant tumor growth, are given as examples of the peptide; in particular, RGD peptides are given as examples thereof. By using an RGD peptide as the target binding site, particle compositions, which are capable of specifically recognizing a diseased portion, and pharmaceutical compositions using the particle compositions, are obtainable. RGD peptides as used herein refer to peptides that include an arginine-glycine-aspartic acid (RGD) sequence. The RGD peptide is preferably a cyclic RGD (cRGD) peptide. In particular, the peptide represented by the following formula is given as an example of the cRGD peptide contained in each of the block copolymers represented by formulas (3) and (4).

[Chem. 4]

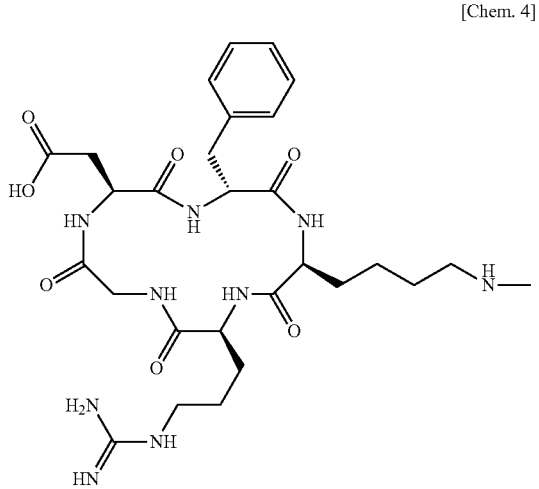

Any appropriate group may be used as the linking group between the target binding site and the hydrophilic polymer of the drug carrier; for example, any amino acid residue is given as an example thereof.

Any appropriate method may be employed as the manufacturing method for the drug carrier having a target binding site. For example, the method may be: preparing the drug carrier represented by formula (1) or (2) in advance, acetalizing the terminus of the hydrophilic polymer side thereof, and mixing it in an acidic solution with a desired compound having a target binding site and a cysteine terminus; or, acetalizing the terminus of the hydrophilic polymer side of a block copolymer having a hydrophilic polymer and a polyamino acid that does not have a particular cyclic structure or a cation-containing group in its side chains; mixing it in an acidic solution with a desired compound having a target binding site and a cysteine terminus to bind the target binding site to the terminus of the hydrophilic polymer, and then introducing a particular cyclic structure and cation-containing group into the side chains of the polyamino acid by substitution or conversion.

B-2. Target Binding Carrier

The target binding carrier is obtained, for example, by binding a compound having a target binding site to the hydrophilic polymer chain of a block copolymer having a hydrophilic polymer chain and a hydrophobic polymer chain. In accordance with a particle composition that further includes a target binding carrier, in addition to improving delivery of the drug to the desired target site, by designing the drug carrier so as to have a molecular weight of several tens of thousands or less, in case the particle collapses before being delivered to the target site, the drug carrier can be eliminated from the body through metabolism, and damage caused by unnecessary gene transfer into normal cells (non-target cells) can be avoided. In particular, block copolymers represented by the following formula (I) or (II) are given as examples of the block copolymer having a hydrophilic polymer chain and a hydrophobic polymer chain.

[Chem. 5]

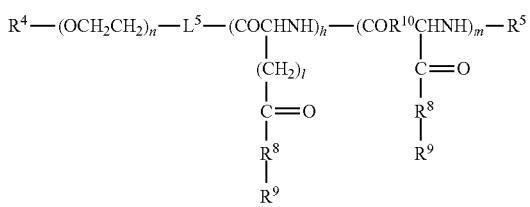

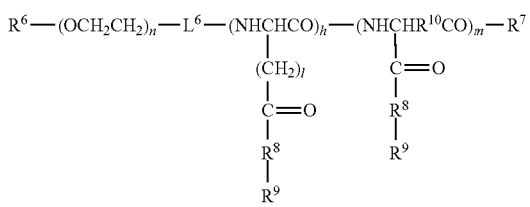

In the general formula (I) and the general formula (II): $R^4$ and $R^6$ each independently represent a hydrogen atom or a group represented by $R^{11}(R^{12})CH(CH_2)_k$— (Provided that $R^{11}$ and $R^{12}$: (i) each independently represent a hydrogen atom, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkylsiloxy group, a siloxy group, or a silylamino group; (ii) are identical to each other and each form a $C_{1-3}$ alkyl group-substituted or unsubstituted ethylenedioxy group or propylenedioxy group; or (iii) form a formyl group together with a CH group to which they are bound); k represents an integer of 0 to 10;

$R^5$ represents a hydrogen atom, a saturated or unsaturated $C_1$ to $C_{29}$ aliphatic carbonyl group, or an aryl carbonyl group;

$R^7$ represents a hydroxyl group, a saturated or unsaturated $C_1$ to $C_{30}$ aliphatic oxy group or an aryl-lower alkyloxy group;

$R^8$ represents —O— or —NH—;

$R^9$ represents a hydrogen atom, a phenyl group, a benzyl group, a —$(CH_2)_4$-phenyl group, an unsubstituted or amino group- or carbonyl group-substituted $C_4$ to $C_{16}$ alkyl group, or a residue of a sterol derivative;

$R^{10}$ represents a methylene group;

n represents an integer in the range of 55 to 4,600;

h represents an integer in the range of 10 to 200;

m represents an integer in the range of 0 to 200 (provided that: when m represents 1 or more, the binding order of (a) (COCHNH) unit (s) and (a) ($COR^{10}CHNH$) unit(s) is arbitrary, and the binding order of (an) (NHCHCO) unit(s) and (an) ($NHCHR^{10}CO$) unit(s) is arbitrary; and when m represents 2 or more, $R^9$'s are each independently selected in each amino acid unit in one block copolymer, and are present at random, but $R_9$ which represents a hydrogen atom accounts for 75% or less of the total of $R^9$'s);

i represents 1 or 2;

$L^5$ represents a linking group selected from —NH—, —O—, —O-$M^1$-NH—, —CO—, —$CH_2$—, and —O-$M^1$-S-$M^1$-NH— (where $M^1$'s each independently represent a $C_1$ to $C_6$ alkylene group); and $L^6$ represents a linking group selected from —OCO-$M^2$-CO— and —NHCO-$M^2$-CO— (provided that $M^2$ represents a $C_1$ to $C_6$ alkylene group).

Preferably, n represents an integer of 110 or more, more preferably an integer of 180 or more. Further, n preferably represents an integer of 460 or less, more preferably an integer of 340 or less.

Preferably, h represents an integer of 20 or more. Further, h preferably represents an integer of 100 or less, more preferably an integer of 60 or less.

Preferably, m represents an integer of 100 or less, more preferably an integer of 60 or less.

With respect to the compound having the target binding site, it can bind a compound having any target binding site that depends on the targeted tissue and purpose; for example, the compounds exemplified in section B-1 are given as examples thereof. The hydrophilic polymer chain of the target binding carrier and the compound having the target binding site may be bound to each other directly or via any linking group. For example, when $R^4$ or $R^6$ in the block copolymer represented by the formula (I) or (II) represents a group represented by $R^{11}(R^{12})CH(CH_2)_k$—, the hydrophilic polymer chain can bind to the compound having the target binding site via this group.

From the viewpoint of avoiding unnecessary gene transfer into normal cells and the damage resulting therefrom, it is preferred to select, as the target binding carrier, a carrier having a target binding site, which is a block copolymer having a weak binding force to nucleic acid as compared to the drug carrier (e.g., a block copolymer having an electrically neutral or anionic hydrophobic segment moiety).

C. Pharmaceutical Composition

Pharmaceutical compositions of the present invention include the particle composition and the drug encapsulated in the particle composition. The drug carrier included in the particle composition can form a complex (e.g., a PIC) with a biopolymer as the drug to be encapsulated. Thus, the pharmaceutical compositions of the present invention include the complex. The complex can be formed in a relatively easy manner by utilizing the effect of the amino acid segment having a cation-containing group (e.g., under physiological conditions). On the other hand, even in the case of a drug carrier free of an amino acid segment having a cation-containing group (e.g., an embodiment in which the percentage of the amino acid segment having the cyclic structures is 100%), the complex can be formed without utilizing the effect of the cation-containing group by setting its formation environment to an acidic condition (e.g., pH 5 or less, or, for example, pH 4 or less).

As the above-mentioned drug, anionic compounds having more negative charge than positive charge in an aqueous medium having a physiological pH (e.g., pH 7.4), and cationic compounds having more positive charge than negative charge in the aqueous medium can be given as examples. The drug is preferably a biopolymer from the viewpoint that it can suitably form a complex with the drug carrier. The biopolymer as used herein refers to polymers derived from a living organism and polymers having a structure similar thereto; in particular, proteins, lipids, and nucleic acids can be given as examples thereof. The biopolymer is preferably at least one kind selected from the group consisting of proteins and nucleic acids. Proteins as used herein encompass peptides.

Nucleic acid means poly- or oligonucleotides including as basic units nucleotides each formed of a purine or pyrimidine base, a pentose, and phosphoric acid; oligo- or poly-double-stranded RNA, oligo- or poly-double-stranded DNA, oligo- or poly-single-stranded DNA, and oligo- or poly-single-stranded RNA can be given as examples thereof. Further, oligo- or poly-double-stranded nucleic acid and oligo- or poly-single-stranded nucleic acid, in each of which RNA and DNA exist in a mixed state in the same strand, are also included. Further, the nucleotide contained in the nucleic acid may be a natural type or a chemically modified non-natural type, or may have added thereto an amino group, a thiol group, a fluorescent compound, or any other molecule. Although it is not limiting, the nucleic acid may be comprised of 4 to 20,000 bases, preferably 10 to 10,000 bases, more preferably 18 to 30 bases. Further, in consideration of functions or effects, plasmid DNA, siRNA, micro RNA, mRNA, shRNA, antisense nucleic acid, decoy nucleic acid, aptamers, and ribozymes can be given as examples.

In case the nucleic acid is siRNA, the mixing ratio between the particle composition and the siRNA may be set to any appropriate ratio. For example, the ratio (N/P ratio) between the total number (N) of cationic groups (in practice, primary to quaternary amino groups, an amidine group, an imidine group, and groups represented by formulas (i) to (iv) contained in the polyamino acid segment) in the drug carrier forming the particle composition and the total number (P) of phosphate groups in the nucleic acid is preferably 0.5 to 100, more preferably 0.5 to 10, still more preferably 1 to 10. When the N/P ratio falls within the above-mentioned range, a stable complex having a small amount of a free polymer can be prepared, and a high prevalence in vivo can be obtained. It should be noted that the cationic group (N) refers to a group capable of electrostatically interacting with a phosphate group in a nucleic acid to be encapsulated to form an ionic bond.

The size of the complex may be set to any appropriate size depending on the purpose. For example, the complex preferably has an average particle diameter of 5 nm to 200 nm, more preferably 10 nm to 100 nm, which is measured by the dynamic light scattering measurement method (DLS).

A particle composition encapsulating a drug may be prepared, for example, by stirring a mixed solution of a drug carrier and a drug while applying energy by ultrasonic irradiation. Further, the complex may be prepared, for example, by mixing siRNA and a particle composition in any buffer (e.g., a Iris buffer). The mixing step is preferably performed in a sufficiently reductive state so as to prevent only the block copolymers constituting the particle composition from aggregating by forming disulfide bonds before the formation of ionic bonds between the block copolymers and siRNA. The reductive conditions may be adjusted, for example, by adding dithiothreitol (DTT).

EXAMPLES

Hereinafter, the present invention will be described more specifically by way of examples. However, the present invention is not limited by these examples. It should be noted that analysis methods for each characteristic in the examples are as described below unless otherwise specified.

(1) Nuclear Magnetic Resonance Spectrum ($^1$H-NMR)

Measurements were performed with a nuclear magnetic resonance apparatus (manufactured by JEOL Ltd., JEOL AL300 (300 MHz)) under the conditions of: solvent: DMSO-d6, and measurement temperature: 25° C.

(2) Measurement of the Content of the Amino Acid Segment having the Cyclic Structures and the Amino Acid Segment having the Cation-Containing Group(s) (Iminothiolane Substitution Ratio)

Calculations were performed based on the peak intensity ratio between β-, γ-, and δ-methylene protons (($CH_2)_3$, δ=1.3 to 1.9 ppm) of lysine and a trimethylene unit (HS—$(CH_2)_3$, δ=2.1 to 2.8 ppm) of a mercaptopropyl group in the $^1$H-NMR spectrum.

(3) Structure Determination of the Polyamino Acid Segment in the Block Copolymer (3-1) Measurement of Thiol Group Content The block copolymer solution (5 mg/mL) obtained in Example 1 was incubated in a 10 mM HEPES buffer (containing 5 mM EDTA and 15 mM DTT) at room temperature for 30 minutes and it was reduced. The solution was centrifuged with a Nanosep separation column (molecular weight cut off: 3,000). To the solution after the centrifugation was added a 10 mM HEPES solution (containing 5 mM EDTA), and the mixture was centrifuged again (concentration/washing step). The concentration/washing step was performed three times. After the final centrifugation, the concentrated polymer solution was collected and diluted by adding a 10 mM HEPES solution (containing 5 mM EDTA). A flow-through fraction was also collected and subjected to the same treatment. Those fractions were placed on ice and kept at a solution temperature of 0 to 4° C. until Ellman's reagent was added.

Each of the polymer fraction and flow-through fraction after the treatment was measured for its absorbance at a wavelength of 412 nm by Ellman's method. A free thiol content was determined based on a calibration curve for glutathione and the final thiol content of the polymer fraction obtained by subtracting the thiol content of the flow-through fraction corrected with the remaining amount of DTT.

(3-2) Measurement of Primary Amino Group Content

The block copolymer solution (5 mg/mL) obtained in Example 1 was diluted with 0.1 M sodium bicarbonate (pH 8.2) to afford a polymer solution at 0.09 mM (PEG-PLL) or 0.9 mM (Example 1) in terms of lysine unit molar concentration. A 2,4,6-trinitrobenzenesulfonic acid (TNBSA) solution (5 wt/vol % solution in MeOH) was diluted with 0.1 M sodium bicarbonate (pH 8.2) to prepare a 0.34 mM TNBSA solution. The polymer solution and the TNBSA solution were mixed with each other at a volume ratio of 2:1 (polymer solution:TNBSA solution) and incubated at 37° C. for 2 hours. After the incubation, the sample was left to stand still for 15 minutes so that the temperature returned to room temperature, and then measured for its absorbance at 354 nm with a spectrophotometer (NanoDrop ND-1000).

(3-3) Measurement of Cyclic Structure Content

Calculations were performed by subtracting the thiol group content obtained in (3-1) and the primary amino group content obtained in (3-2) from the number of units in the resultant block copolymer.

Synthesis Example 1

Synthesis of acetal-polyethylene glycol-poly(L-lysine) Block Copolymer (acetal-PEG-PLL)

1.20 g of acetal-PEG-$NH_2$ having an average molecular weight of 12,000 and 2.90 g of thiourea were dissolved in 18 mL of N,N-dimethylformamide (DMF). Next, to the solution was added a solution obtained by dissolving 1.34 g of ε-trifluoroacetyl-L-lysine N-carboxylic anhydride (Lys (TFA)-NCA, 50 equivalents relative to acetal-PEG-$NH_2$) in 20.1 mL of DMF, and the mixture was allowed to react at 20° C. for 2 days. The reaction solution was added dropwise to 600 mL of a mixed solvent of diethyl ether-methanol (15/1) to afford a white precipitate. Then, an operation involving dissolving the precipitate in methanol and adding the solution dropwise to diethyl ether was repeated twice. The resultant white precipitate was filtered and dried under vacuum to afford 2.22 g of acetal-PEG-PLL(TFA).

2.00 g of the resultant acetal-PEG-PLL(TFA) were dissolved in 200 mL of methanol. To the solution were added 20 mL of a 1 N sodium hydroxide solution, and the mixture was allowed to react at 35° C. for 12 hours. The reaction solution was charged into a dialysis tube (manufactured by Funakoshi Corporation, Spectra/Por, molecular weight cut off: 6,000 to 8,000) and dialyzed four times against a solution of 150 mM NaCl in a 10 mM phosphate buffer (pH 7.4) as the external solution and subsequently three times against pure water as the external solution. The solution inside the dialysis membrane was collected and lyophilized to afford 1.63 g of acetal-PEG-PLL as a white solid. $^1$H-NMR confirmed that the resultant compound was a product of interest. The polylysine segment of the resultant acetal-PEG-PLL had a degree of polymerization of 45.

Synthesis Example 2

Synthesis of cRGD-PEG-PLL 26.2 mg of a cRGD peptide (5-fold equivalents relative to the acetal-PEG-PLL) were dissolved in 1 mL of a 10 mM phosphate buffer (pH 7.4). Next, to the solution were added 5 mg (1 equivalent relative to the cRGD peptide) of dithiothreitol (DTT), and the mixture was stirred at 25° C. for 30 minutes to reduce the cRGD peptide. In another vessel, 125 mg (1 equivalent) of the acetal-PEG-PLL obtained in Synthesis Example 1 were dissolved in a 0.2 M sodium acetate buffer (pH 4.0), and to the stirred solution was added dropwise the reduced cRGD peptide solution. The reaction was performed with stirring at 25° C. for 4 days. The reaction solution was transferred to a dialysis tube (manufactured by Funakoshi Corporation, Spectra/Por, molecular weight cut off: 6 to 8 K) and dialyzed against a solution of 150 mM NaCl in a 10 mM phosphate buffer (pH 7.4) for 2 days and then against distilled water for 2 days. The dialysate was treated with a filter (Japan Millipore Corporation, Sterivex™ GP 0.22 μm) and then lyophilized to afford cRGD-PEG-PLL as white powder (yield: 112 mg, 86%). The amount of the cRGD peptide bound to PEG-PLL was calculated based on an integration ratio between a peak of a phenyl CH proton of the cRGD peptide and a $CH_2$ main chain peak of PEG measured by $^1$H-NMR. The resultant cRGD-PEG-PLL had a cRGD introduction ratio of 60%.

Example 1

Synthesis of PEG-PLL(N2IM/IM)

To a reaction vessel were added 89 mg of the acetal-PEG-PLL obtained in Synthesis Example 1 and 2 mL of N-methylpyrrolidone (NMP) containing 5 wt/vol % LiCl. The reaction vessel was filled with argon and capped with a septum. While the reaction vessel was heated, the mixture was stirred to completely dissolve the acetal-PEG-PLL. Next, 178 μL (5 equivalents relative to an amine in lysine of PLL) of N,N-diisopropylethylamine (DIPEA) were added to the solution through the septum under argon.

In the presence of argon, in another vessel, 172 mg of 2-iminothiolane chloride were dissolved in 5 mL of NMP containing wt/vol % LiCl and 250 mM DIPEA (1 equivalent relative to 2-iminothiolane) to prepare a 250 mM 2-iminothiolane solution. In the presence of argon, to the stirred acetal-PEG-PLL solution were added dropwise 2.15 mL of the resultant 2-iminothiolane solution (2.6 equivalents relative to an amine in lysine of PLL), and the mixture was allowed to react at 25° C. for 18 hours. After the reaction, the reaction solution was precipitated in dry diethyl ether in an amount more than 10 times as large as that of the reaction solution to quench the reaction. The precipitate was washed several times with ether and dried under vacuum until the weight became constant to afford a crude product. The resultant crude product was dissolved in a solution of 150 mM NaCl in a 10 mM phosphate buffer (pH 6.0). After that, the solution was transferred to a dialysis tube (manufactured by Funakoshi Corporation, Spectra/Por 7, molecular weight cut off: 10 kDa) and dialyzed against a solution of 150 mM NaCl in a 10 mM phosphate buffer (pH 6.0) for 1 day (the external solution was exchanged three times) and against distilled water for 1 day (the external solution was exchanged three times). The dialysate was treated with a filter (Japan Millipore Corporation, Sterivex™ GP 0.22 μm) and then lyophilized to afford acetal-PEG-PLL (N2IM/IM) as white powder (yield: 99 mg, 85%). The resultant PEG-PLL (N2IM/IM) had an iminothiolane substitution ratio of 95%. Table 1 shows the iminothiolane substitution ratio and the cyclic structure content of the resultant block copolymer.

Example 2

Synthesis of cRGD-PEG-PLL(N2IM/IM)

To a reaction vessel were added 55 mg (1 equivalent) of the cRGD-PEG-PLL obtained in Synthesis Example 2 and 5 mL of NMP containing 5 wt/vol % LiCl. The reaction vessel was filled with argon and then capped with a septum. While the reaction vessel was heated, the mixture was stirred to completely dissolve the cRGD-PEG-PLL. Next, 252 μL of DIPEA (11.8 equivalents relative to an amine in lysine contained in PLL) were added to the solution through the septum under argon (solution 1). In the presence of argon, in another vessel, 106 mg of 2-iminothiolane chloride were dissolved in 7.86 mL of NMP containing 5 wt/vol % LiCl and 134 μL of DIPEA (1 equivalent relative to 2-iminothiolane) to prepare a 96 mM 2-iminothiolane solution (solution 2). In the presence of argon, to the stirred solution 1 (cRGD-PEG-PLL solution) were added dropwise 3 mL of the resultant solution 2 (2-iminothiolane solution, 2.35 equivalents relative to an amine in lysine of PLL), and the mixture was allowed to react at 25° C. for 18 hours. After the reaction, the reaction solution was precipitated in dry diethyl ether in an amount more than 10 times as large as that of the reaction solution to quench the reaction. The precipitate was washed several times with ether and dried under vacuum until the weight became constant to afford a crude product. The resultant crude product was dissolved in a solution of 150 mM NaCl in a 10 mM phosphate buffer (pH 6.0). After that, the solution was transferred to a dialysis tube (manufactured by Funakoshi Corporation, Spectra/Por 7, molecular weight cut off: 10 kDa) and dialyzed against a solution of 150 mM NaCl in a 10 mM phosphate buffer (pH 6.0) for 1 day (the external solution was exchanged three times) and against distilled water for 1 day (the external solution was exchanged three times). The dialysate was treated with a filter (Japan Millipore Corporation, Sterivex™ GP 0.22 μm) and then lyophilized to afford cRGD-PEG-PLL (N2IM/IM) as white powder (yield: 61 mg, 85%). The resultant cRGD-PEG-PLL(N2IM/IM) had an iminothiolane substitution ratio of 95%. Table 1 shows the iminothiolane substitution ratio and the cyclic structure content of the resultant block copolymer. It should be noted that the cyclic structure substitution ratio was calculated as a value obtained by multiplying the iminothiolane substitution ratio by 0.9 based on the ratio (1:9) between the thiol group content and the cyclic structure content in the block copolymer of Example 1.

Example 3

Synthesis of cRGD-PEG-PLL(N2IM/IM)

White powder was obtained (yield: 27.3 mg, >95%) in the same manner as in Example 2 except that: the cRGD-PEG-PLL (26.2 mg) obtained in Synthesis Example 2 and DIPEA (58.0 μL, 5.7 equivalents relative to an amine in lysine contained in PLL) were dissolved in NMP (2.7 mL) containing 5 wt/vol % LiCl (solution 1); separately, 2-iminothiolane chloride (187.6 mg) and DIPEA (238 μL) were dissolved in NMP (9.76 mL) containing 5 wt/vol % LiCl, and then part of the solution was diluted to ⅓ to prepare a 45.0 mM 2-iminothiolane solution (solution 2); and 1 mL (0.78 equivalent relative to an amine in lysine of PLL) of the solution 2 was added dropwise to 2.7 mL of the solution 1. The iminothiolane substitution ratio of the resultant cRGD-PEG-PLL(N2IM/IM) was calculated in the same manner as in Example 2. The resultant cRGD-PEG-PLL(N2IM/IM) had an iminothiolane substitution ratio of 45%. Table 1 shows the iminothiolane substitution ratio and the cyclic structure content of the resultant block copolymer.

Comparative Example 1

Synthesis of cRGD-PEG-PLL(N2IM/IM)

White powder was obtained (yield: 27.3 mg, >95%) in the same manner as in Example 2 except that: the cRGD-PEG-PLL (25.7 mg) obtained in Synthesis Example 2 and DIPEA (49.8 μL, 5 equivalents relative to an amine in lysine contained in PLL) were dissolved in NMP (2.6 mL) containing 5 wt/vol % LiCl (solution 1); separately, 2-iminothiolane chloride (187.6 mg) and DIPEA (238 μL) were dissolved in NMP (9.76 mL) containing 5 wt/vol % LiCl, and then part of the solution was diluted to 1/10 to prepare a 13.6 mM 2-iminothiolane solution (solution 2); and 1 mL (0.24 equivalent relative to an amine in lysine of PLL) of the solution 2 was added dropwise to 2.6 mL of the solution 1. The iminothiolane substitution ratio of the resultant cRGD-PEG-PLL(N2IM/IM) was calculated in the same manner as in Example 2. The resultant cRGD-PEG-PLL(N2IM/IM) had an iminothiolane substitution ratio of 15%. Table 1 shows the iminothiolane substitution ratio and the cyclic structure content of the resultant block copolymer.

Comparative Example 2

Synthesis of PEG-PLL(DTBP)

To a reaction vessel were added 300 mg of the acetal-PEG-PLL obtained in Synthesis Example 1 and 60 mL of a 100 mM borate buffer (pH 9.0). 439 mg (2 equivalents relative to a lysine unit) of dimethyl 3,3'dithiobispropionimidate dihydrochloride (DTBP) were dissolved in the resultant polymer solution. After having been allowed to react with stirring at room temperature for 45 minutes, the solution was transferred to a Slide-A-Lyzer cassette (molecular weight cut off: 3.5 kDa) and subjected to dialysis treatment against a solution of 150 mM NaCl in a 10 mM phosphate buffer (pH 7.4) for 1.5 hours. After the dialysis, 300 mg of DTT were added. After having been allowed to react at room temperature for 30 minutes, the mixture was transferred to a Slide-A-Lyzer cassette (molecular weight cut off: 3.5 kDa) and subjected to dialysis treatment against a solution of 150 mM NaCl in a 10 mM phosphate buffer (pH 6.0) for 1.5 hours and against pure water for 1.5 hours. The dialysate was treated with a filter (Japan Millipore Corporation, Sterivex™ GP 0.22 μm) and then lyophilized to afford acetal-PEG-PLL (DTBP) as white powder (yield: 299 mg, 73%). The resultant PEG-PLL (DTBP) had a DTBP substitution ratio of 95%. Table 1 shows the iminothiolane substitution ratio and the cyclic structure content of the resultant block copolymer.

TABLE 1

| Block copolymer | Kind | Imino-thiolane substitution ratio (%) | Cyclic structure content (%) |
|---|---|---|---|
| Example 1 | PEG-PLL(N2IM/IM) | 95 | 86 |
| Example 2 | cRGD-PEG-PLL(N2IM/IM) | 95 | 86 |
| Example 3 | cRGD-PEG-PLL(N2IM/IM) | 45 | 41 |
| Comparative Example 1 | cRGD-PEG-PLL(N2IM/IM) | 15 | 14 |
| Comparative Example 2 | PEG-PLL(DTBP) | 0 | 0 |
| Comparative Example 3 | cRGD-PEG-PLL* | 0 | 0 |

*block copolymer obtained in Synthesis Example 2

Test Example 1

Preparation of Complex

The siRNAs used for the preparation of the below-described complexes are as described below. Labels such as Cy5 were introduced into the 5'-terminus of each sense strand. These siRNAs are available from Hokkaido System Science Co., Ltd.

(1) GL3-siRNA (siRNA against firefly luciferase):

```
Sense strand:
                                  (SEQ ID NO: 1)
5'-CUUACGCUGAGUACUUCGAdTdT-3'

Antisense strand:
                                  (SEQ ID NO: 2)
5'-UCGAAGUACUCAGCGUAAGdTdT-3'
```

(2) scramble-siRNA (siRNA having a non-therapeutic sequence):

```
Sense strand:
                                  (SEQ ID NO: 3)
5'-UUCUCCGAACGUGUCACGUdTdT-3'

Antisense strand:
                                  (SEQ ID NO: 4)
5'-ACGUGACACGUUCGGAGAAdTdT-3'
```

(3) hVEGF-siRNA (siRNA against human vascular endothelial growth factor):

```
Sense strand:
                                  (SEQ ID NO: 5)
5'-GAUCUCAUCAGGGUACUCCdTdT-3'

Antisense strand:
                                  (SEQ ID NO: 6)
5'-GGAGUACCCUGAUGAGAUCdTdT-3'
```

(4) mVEGFR2-siRNA (siRNA against mouse vascular endothelial growth factor):

```
Sense strand:
                                  (SEQ ID NO: 7)
5'-AUGCGGCGGUGGUGACAGUdTdT-3'

Antisense strand:
                                  (SEQ ID NO: 8)
5'-ACUGUCACCACCGCCGCAUdTdT-3'
```

Each of the PEG-PLL(N2IM/IM) obtained in Example 1, the cRGD-PEG-PLL(N2IM/IM) obtained in Examples 2 and 3 and Comparative Example 1, the PEG-PLL(DTBP) obtained in Comparative Example 2, and the cRGD-PEG-PLL having an unmodified PLL side chain (prepared in Synthesis Example 2) as Comparative Example 3 was dissolved in a 10 mM HEPES buffer (pH 7.4) so as to have a concentration of 5 mg/mL. Next, the solution was mixed with a 10 mM HEPES buffer (pH 7.4) having a DTT concentration of 30.54 mg/mL to adjust the concentration so that the N/P ratio was 1 to 8, and the mixture was left to standstill at room temperature for 30 minutes. siRNA was dissolved in a 10 mM HEPES buffer (pH 7.4) to prepare a 15 μM siRNA solution. The siRNA solution was mixed with the PEG-PLL(N2IM/IM) solution, the cRGD-PEG-PLL(N2IM/IM) solution, the PEG-PLL(DTBP) solution, or the cRGD-PEG-PLL solution at a volume ratio of 2:1, and the mixture was left to stand still at 25° C. for 24 hours. The resultant solution was transferred to a Slide-A-Lyzer cassette (molecular weight cut off: 3.5 kDa) and dialyzed against a 10 mM HEPES solution (pH 7.4) containing 5 v/v % DMSO for 2 days and against a 10 mM HEPES solution (pH 7.4) for 2 days to afford a micelle encapsulating siRNA as a complex of the block copolymer and the siRNA. The "N/P ratio" as used herein means (the concentration of polyamino acid units in the block copolymer)/(the concentration of phosphate groups in the nucleic acid). Table 2 shows the produced micelles encapsulating siRNA.

TABLE 2

| Micelle encapsulating siRNA | Block copolymer | siRNA |
|---|---|---|
| 1 | Example 2 | GL3-siRNA |
| 2 | Example 3 | GL3-siRNA |
| 3 | Example 2 | hVEGF-siRNA |
| 4 | Example 2 | mVEGFR2-siRNA |
| 5 | Example 1 | GL3-siRNA |
| C-1 | Comparative Example 1 | GL3-siRNA |
| C-2 | Comparative Example 2 | GL3-siRNA |
| C-3 | Comparative Example 3 | GL3-siRNA |
| R-1 | Example 2 | scramble siRNA |

Test Example 2

Evaluation of the Physical Properties of the Micelle Encapsulating siRNA

With regard to micelle 1 encapsulating siRNA, the histograms of the micelle encapsulating siRNA for a polydispersity index (PDI), a cumulant particle diameter, and a particle diameter distribution were measured by a dynamic light scattering method (DLS) using Zetasizer Nano ZS (manufactured by Malvern). The histogram of the particle diameter distribution was determined with the accompanying software. FIG. 1 shows the histogram of the particle diameter distribution.

The results of the DLS analysis of the micelle 1 encapsulating siRNA revealed that the cumulant particle diameter was 41 nm, and the PDI was 0.09, indicating that particles of a narrow variance were obtained.

Test Example 3

Evaluation of the Stability of the Micelle Encapsulating siRNA

Figure 2:
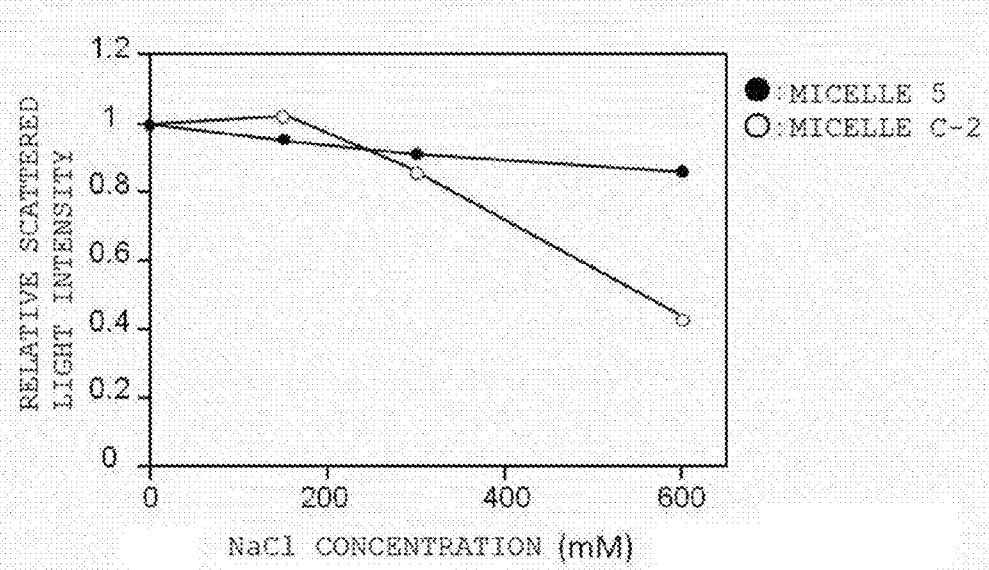
FIG. 2 is a graph showing scattered light intensity at each ion concentration of a complex according to the present invention.

Micelle 5 encapsulating siRNA and an NaCl solution having a concentration of interest (NaCl concentration: 150 mM, 300 mM, or 600 mM) were mixed with each other at a volume ratio of 1:1, and incubated at 37° C. for 24 hours. The solution after the incubation was measured for its scattered light intensity with Zetasizer Nano ZS (manufactured by Malvern). Similarly, micelle C-2 encapsulating siRNA was also measured for its scattered light intensity. FIG. 2 shows the scattered light intensities at each NaCl concentration.

In general, a PIC micelle dissociates in accordance with an increase in ionic strength, and hence the scattered light intensity decreases in accordance with an increase in ionic strength. Micelle 5 encapsulating siRNA showed a small reduction in scattered light intensity even at a high ionic strength (NaCl concentration: 600 mM), indicating that the micelle encapsulating siRNA had a stable structure. On the other hand, micelle C-2 encapsulating siRNA using the block copolymer having no cyclic structure showed a reduction in scattered light intensity in accordance with an increase in ionic strength.

Test Example 4

Evaluation of the Amount of siRNA taken up into Cells

Figure 3:
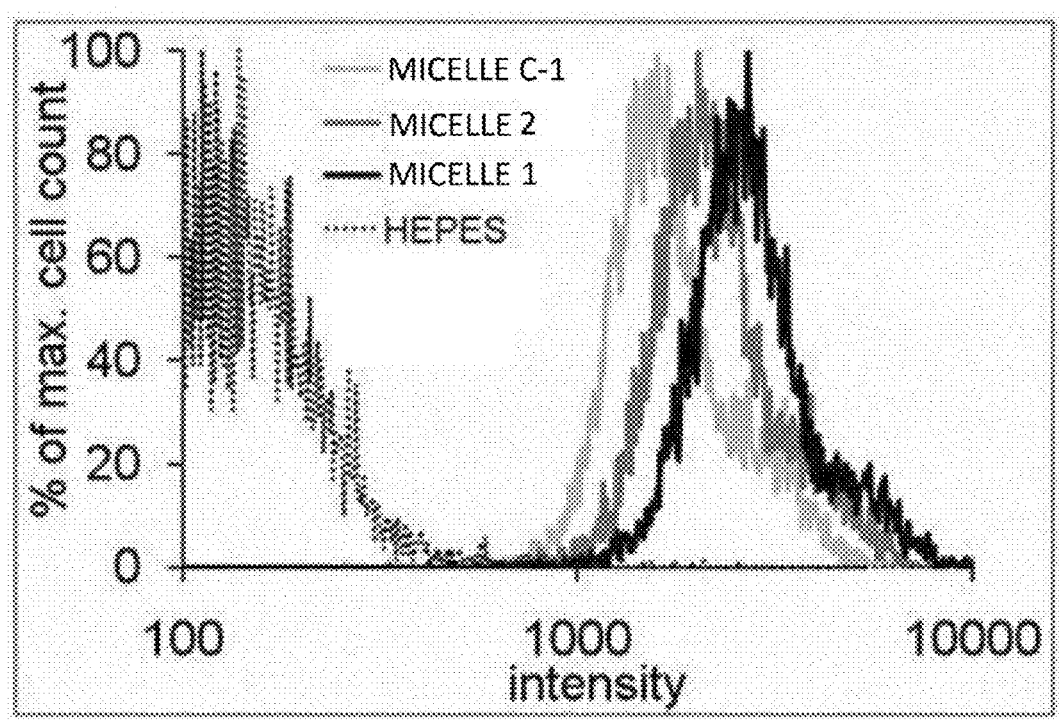
FIG. 3 is a graph showing amounts of siRNA taken up into cells incubated together with complexes according to the present invention.

HeLa cells were seeded in a 6 well dish at 50,000 cells/well and incubated for 24 hours in an incubator with a DMEM medium containing 10% fetal bovine serum. The medium was exchanged for a fresh DMEM medium containing 10% fetal bovine serum, and each of micelles 1, 2 and C-1 encapsulating siRNA was added to the medium so that the concentration of Cy5-siRNA was 300 nM/well. After having been incubated in an incubator at 37° C. for 2 hours, the cells were washed three times with 1 mL of a PBS buffer, and the cells were detached from the dish with a trypsin-EDTA solution. The detached cells were subjected to histogram analysis using a flow cytometer (manufactured by BD, LSRII) in which a Cy5 filter was set. Thus, the amount of siRNA taken up into the cells was evaluated. FIG. 3 shows a graph showing the amount of siRNA taken up into the cells.

In each of the micelles encapsulating siRNA, the transfer of encapsulated siRNA into the cells was confirmed. In this case, the micelle encapsulating siRNA using the block copolymer having a cyclic structure content of 40% or more showed a remarkably high intensity and was particularly excellent in transfer into the cells.

Test Example 5

Evaluation of RNAi Activity

Figure 4:
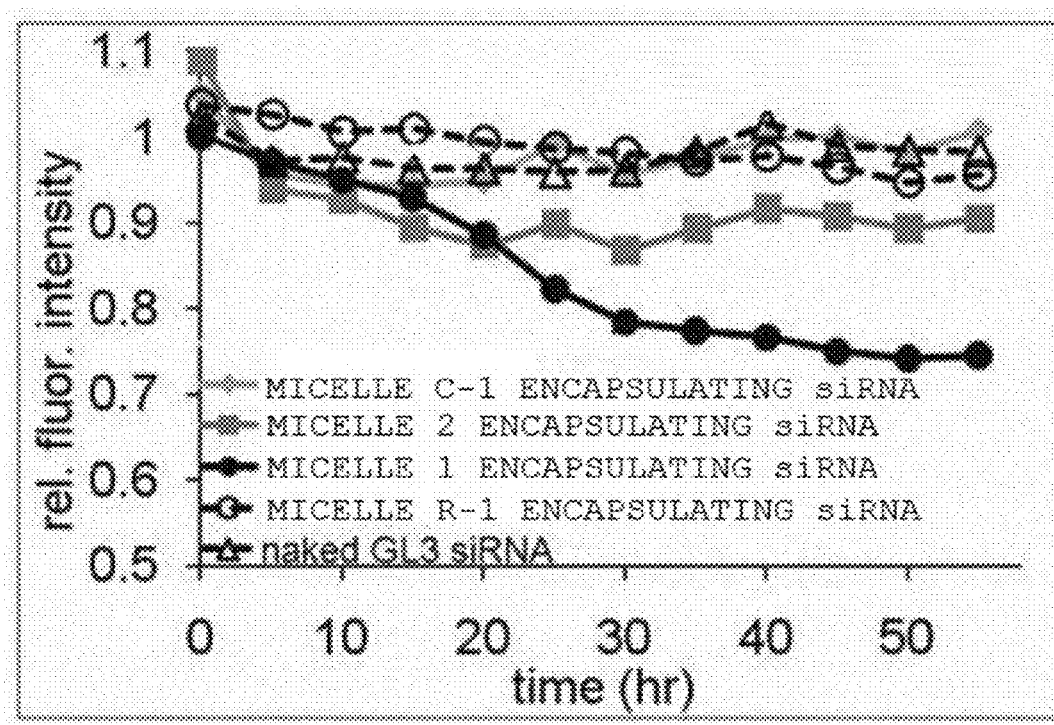
FIG. 4 is a graph showing RNAi activity of complexes according to the present invention.

Luciferase-expressing HeLa (HeLa-Luc) cells were seeded in a 35 mm plate at 50,000 cells/plate and incubated in an incubator with a DMEM medium containing 10% fetal bovine serum for 24 hours. The medium was exchanged for a fresh DMEM medium containing 10% fetal bovine serum, and each of micelles 1, 2, C-1, and R-1 encapsulating siRNA (containing 10 μM siRNA) was added to the medium so that the concentration of siRNA was 200 nM, and then a luciferin substrate was added so that the concentration was 100 μM. For comparison, naked GL3 siRNA was added to the medium so that the concentration was 200 nM, and then the luciferin substrate was added so that the concentration was 100 μM. A luciferase luminescence amount was quantified with a real-time cell luminescence measurement apparatus (manufactured by Atto, Kronos) to evaluate an RNAi activity. FIG. 4 shows the results of the resultant luminescence amount expressed as a relative value when a luminescence amount in a plate, in which none of the naked siRNA and micelle solution was administered, was defined as 1. It should be noted that micelle R-1 encapsulating siRNA is the same as micelle 1 encapsulating siRNA except that encapsulated siRNA is siRNA for non-therapeutic use.

Each of micelles 1 and 2 encapsulating siRNA showed a high RNAi activity. The micelle encapsulating siRNA using the block copolymer having a cyclic structure content of 40% or more as described above showed a relatively high RNAi activity.

Test Example 6

Blood Kinetics of Micelle Encapsulating siRNA

Figure 5:
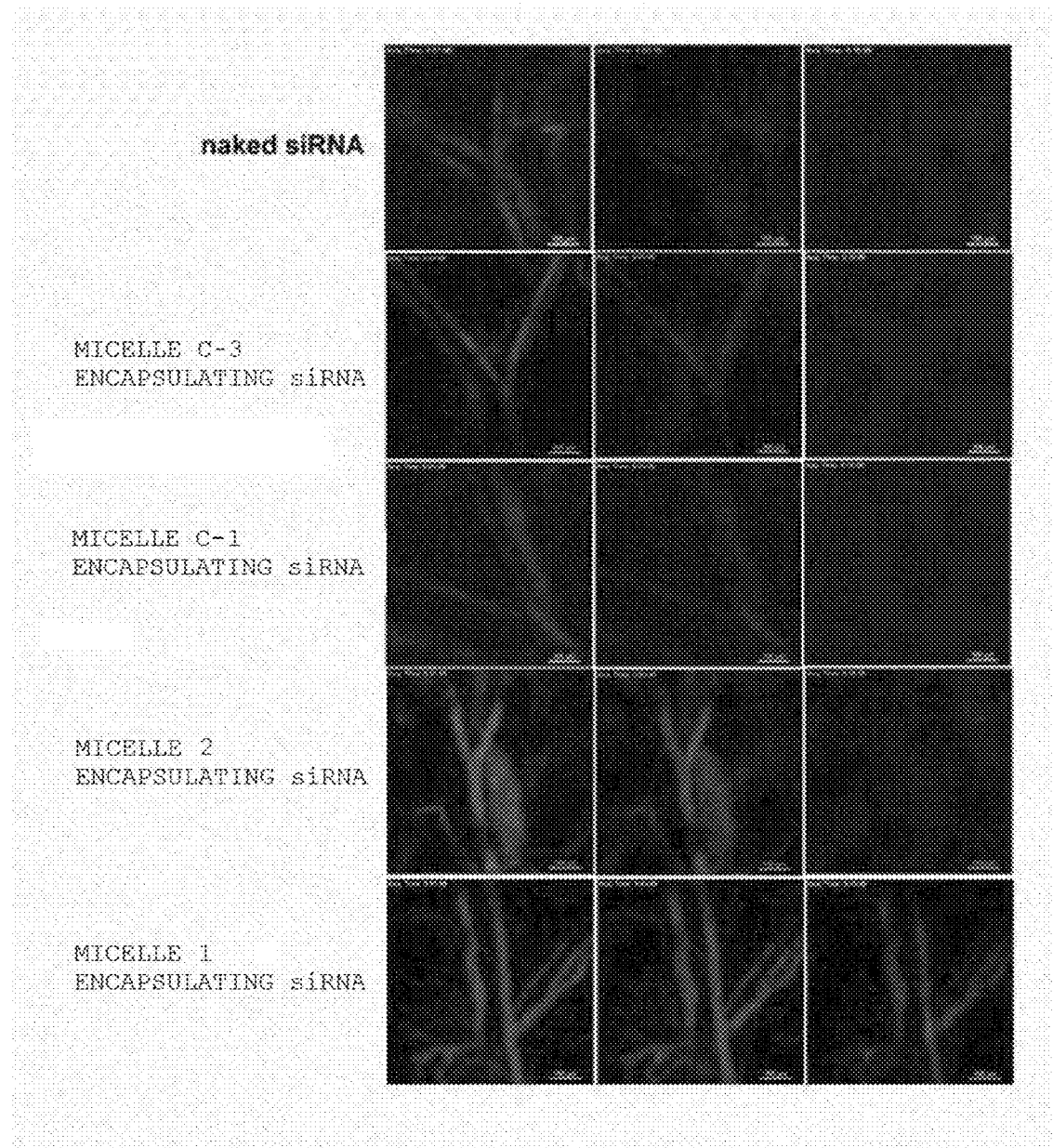
FIG. 5 is in vivo confocal imaging system images, each showing blood kinetics of complexes according to the present invention.

Each of micelles 1, 2, C-1, and C-3 encapsulating siRNA (10 μM siRNA) was administered to the tail veins of mice (Balb/c nude mice, female, 6-week-old) so that the dose was 20 μg of Cy5-siRNA. For comparison, naked Cy5-GL3 siRNA was administered to the tail vein of a mouse (Balb/c nude mice, female, 6-week-old) so that the dose was 20 μg. The blood kinetics of the micelle in the blood vessels of the ears of the mice was observed over time through use of an in vivo confocal imaging system mounted with a high-speed resonant scanner (Nikon A1R, manufactured by Nikon Corporation). FIG. 5 show photographs showing the blood kinetics of the micelle at 1 minute, 3 minutes, and 10 minutes after the administration.

siRNA was confirmed in all the mice at 1 minute after the administration. In micelle 1 encapsulating siRNA using the block copolymer having a high cyclic structure content, the micelle encapsulating siRNA was stably present in blood even at 10 minutes after the administration.

Test Example 7

Evaluation of Anti-Tumor Properties

<Treated Group>

Figure 6:
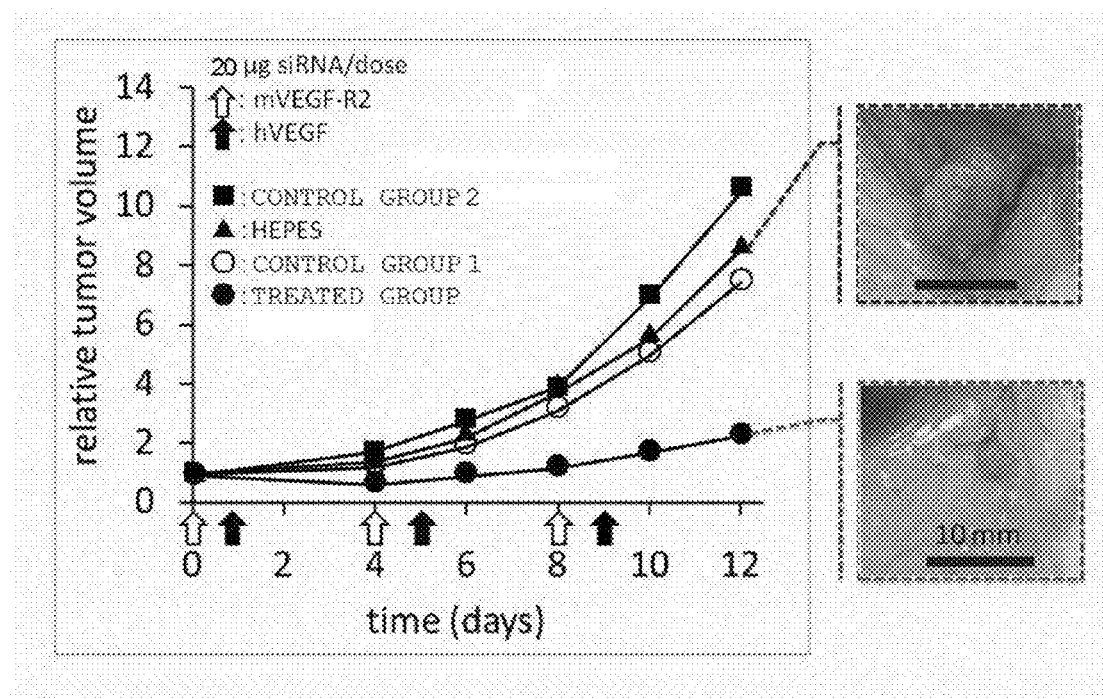
FIG. 6 is a graph and photographs, each showing anti-tumor effects of a complex according to the present invention.

A micelle encapsulating siRNA was administered to the tail vein of a cancer-bearing mouse (Balb/c nude mice, female, 8-week-old, n=4) subcutaneously transplanted with GFP-expressing HeLa (HeLa-GFP) so that the single dose was 20 μg of siRNA. The schedule for the administration was as follows: micelle 3 encapsulating siRNA was administered on the administration start date and 4 days and 8 days after the start of the administration; and micelle 4 encapsulating siRNA was administered 1 day, 5 days, and 9 days after the start of the administration. After the administration, the tumor volume (V=a×b²/2, a=long axis length, b=short axis length) was measured over time. FIG. 6 show a graph showing a relative tumor volume to the tumor volume at the time of the start of the administration, and photographs taken for the state of the tumor after the lapse of 12 days from the start of the administration.

<Control Group 1>

Administration to a cancer-bearing mice (Balb/c nude mice, female, 8-week-old, n=4) subcutaneously transplanted with HeLa-GFP was performed in the same manner as in the treated group except that micelle R-1 encapsulating siRNA was administered on the administration start date and 1 day, 4 days, 5 days, 8 days, and 9 days after the start of the administration. FIG. 6 show a graph showing a relative tumor volume to the tumor volume at the time of the start of the administration.

<Control Group 2>

Administration to cancer-bearing mice (Balb/c nude mice, female, 8-week-old, n=4) subcutaneously transplanted with HeLa-GFP was performed in the same manner as in the treated group except that naked mVEGF-R2 siRNA was administered on the administration start date and 4 days and 8 days after the start of the administration, and naked hVEGF siRNA was administered 1 day, 5 days, and 9 days after the start of the administration, so that the single dose was 20 μg of siRNA. FIG. 6 show a graph showing a relative tumor volume to the tumor volume at the time of the start of the administration.

<Blank Group>

Administration to cancer-bearing mice (Balb/c nude mice, female, 8-week-old, n=4) subcutaneously transplanted with HeLa-GFP was performed in the same manner as in the treated group except that 200 μL of HEPES were administered on the administration start date and 1 day, 4 days, 5 days, 8 days, and 9 days after the start of the administration. FIG. 6 show a graph showing a relative tumor volume to the tumor volume at the time of the start of the administration, and photographs taken for the state of the tumor after the lapse of 12 days from the start of the administration.

A clear anti-tumor effect was found in the mice of the treated group. No anti-tumor effect was found in the control group 1, in which micelle R-1 encapsulating siRNA as a micelle encapsulating siRNA for non-therapeutic use was used, and the control group 2, in which the naked siRNA was administered.

Test Example 8

Evaluation of Tumor Accumulation Properties

Figure 7:
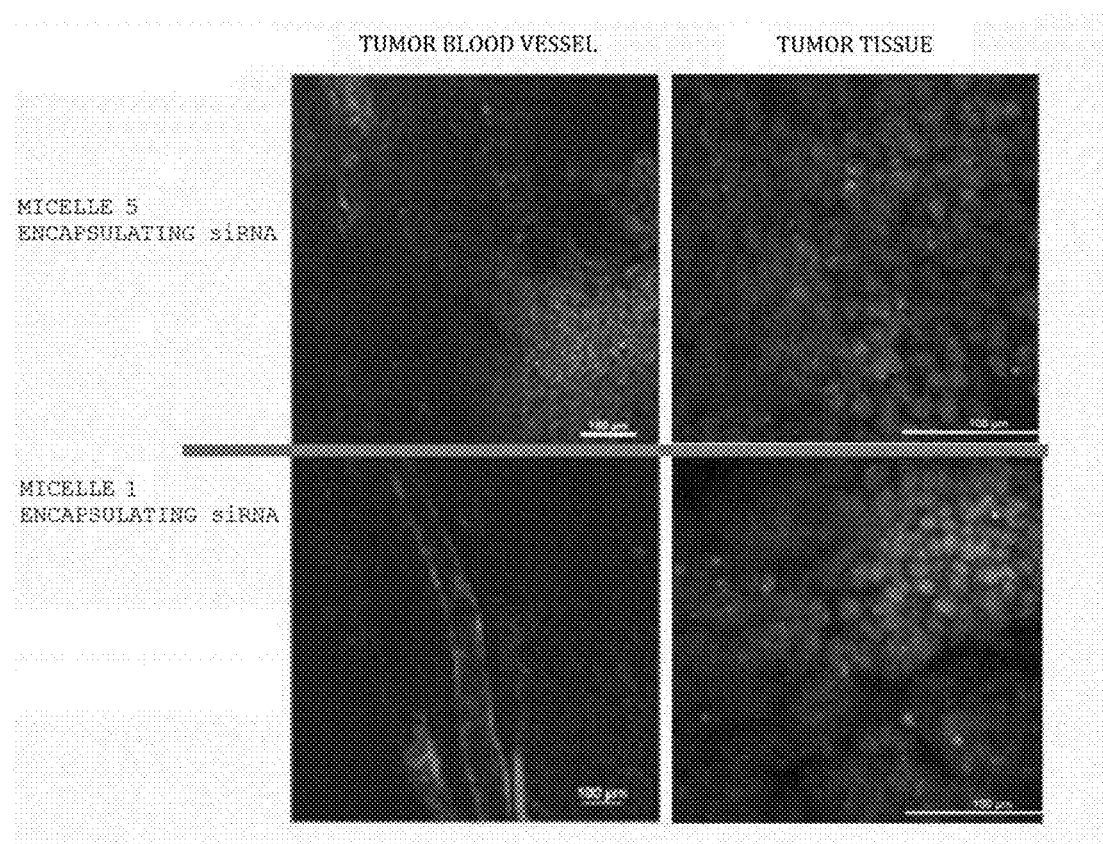
FIG. 7 is in vivo confocal imaging system images, each showing tumor accumulation properties of complexes according to the present invention.
Figure 8:
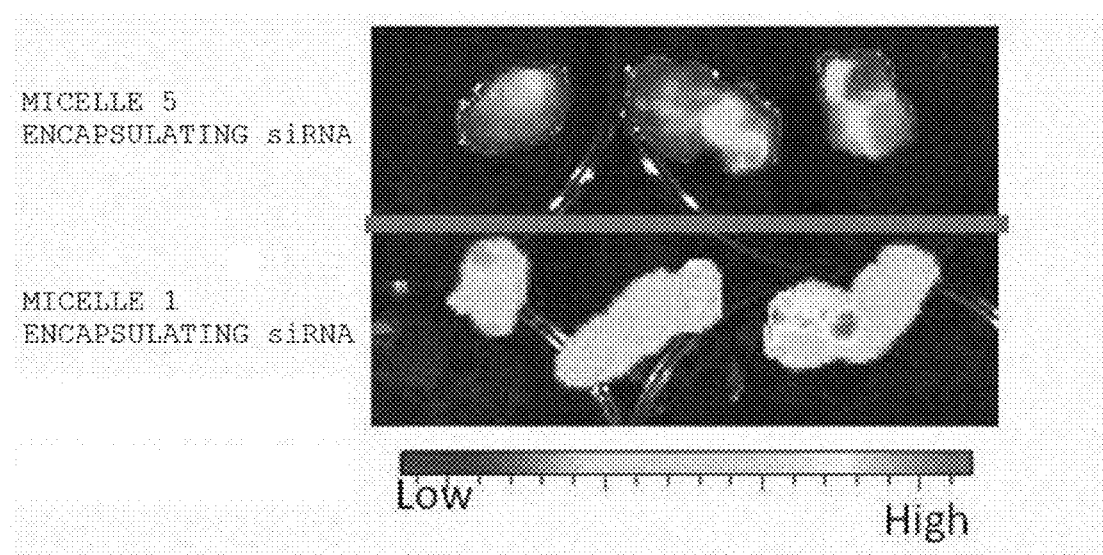
FIG. 8 is IVIS imaging system images of tumors in mice to which complexes according to the present invention have been administered.

Each of micelles 1 and 5 encapsulating siRNA (containing 10 μM siRNA) was administered to the tail vein of a cancer-bearing mouse (Balb/c nude mice, female, 8-week-old) subcutaneously transplanted with GFP-expressing HeLa (HeLa-GFP) so that the dose was 50 μg of Cy5-GL3 siRNA. The accumulation status of the micelle encapsulating siRNA in cancer tissues (perivascular regions and cancer cells) at 24 hours after the administration were observed with an in vivo confocal imaging system (Nikon A1R, manufactured by Nikon Corporation) mounted with a high-speed resonant scanner. After that, the cancer tissues were extirpated, and the accumulation status of the micelle encapsulating siRNA was observed with an IVIS imaging system (manufactured by Xenogen) using a filter for Cy5. FIG. 7 show in vivo confocal imaging system images, and FIG. 8 show IVIS imaging system images.

As a result of the observation with the in vivo confocal imaging system, micelle 1 encapsulating siRNA, which had cRGD disposed on its surface, was accumulated in tumor vessels and cancer cells. Also in the observation of the extirpated cancer cells with the IVIS image system, the micelle encapsulating siRNA showed high accumulation properties in the cancer cells. The results confirmed that the micelle encapsulating siRNA having a target binding site was more likely to be accumulated in tumor vessels and cancer cells than the micelle encapsulating siRNA having no target binding site.

Test Example 9

G-CSF Encapsulation Ratio

About 10 mg of a block copolymer (polylysine segment polymerization degree: 45, iminothiolane substitution ratio: 91%, cyclic structure content: 98%) were weighed in a Spitz tube and dissolved at room temperature by adding purified water so as to achieve a polymer concentration of 5 mg/mL, to thereby afford a polymer solution. The polymer solution was subjected to ultrasonic irradiation (in an ice bath, Low, 1.5 seconds intermittently, 15 minutes) using a biodisruptor (manufactured by NISSEI Corporation, High Power Unit) and then treated with a 0.22 μm membrane filter. Thus, an empty micelle solution having a polymer concentration of 5 mg/mL was obtained. To the empty micelle solution (0.09 mL) was added a 0.3 mg/mL G-CSF solution (0.075 mL) so as to achieve a concentration of 5% (w/w) relative to the polymer. Then, a 200 mM sodium citrate buffer (pH 5) (0.03 mL), a 50% sucrose solution (0.03 mL), and purified water were added therein, and adjustment with 0.1 N HCl (0.05 mL) was performed so as to finally achieve a composition of a polymer concentration of 1.5 mg/mL, a G-CSF concentration of 0.075 mg/mL, and a 20 mM sodium citrate buffer (pH 5). The solution was stirred by inversion two or three times and then left to stand still at 4° C. overnight. The micelle encapsulating G-CSF thus prepared was used and measured for its G-CSF encapsulation ratio by the electrophoresis as described below.

<Measurement Method for G-CSF Encapsulation Ratio>

A sample buffer (manufactured by Bio-Rad Laboratories, Inc., Native Sample Buffer (Cat#161-0738, Lot#310007990)) and the micelle encapsulating G-CSF were mixed with each other at 1:1 (v/v), and 10 μL of the mixture were gently applied to the bottom of a well of an electrophoresis gel (manufactured by Bio-Rad Laboratories, Inc., Mini-PROTEAN® TGX™ Precast Gels (4 to 20%, 12 well comb, Cat#456-1095)). It should be noted that the amount of a marker (manufactured by Bio-Rad Laboratories, Inc., Precision Plus Protein Standard (Cat#1610363, Lot#310008950)) applied was 5 μL. Next, electrophoresis was performed under the following conditions, and while being gently shaken with a shaker, the gel was immersed in a staining solution (manufactured by Bio-Rad Laboratories, Inc., Coomassie Brilliant Blue R250 Staining Solution (Cat#161-0436, Lot#210007039)) for about 15 minutes, and then immersed in a destaining solution (10% acetic acid/40% methanol) for about 10 minutes.

(Electrophoresis Conditions)

Electrophoresis apparatus: Mini Trans-Blot (manufactured by Bio-Rad Laboratories, Inc.)

Electrophoresis buffer (Native): 10×Tris/Glycine Buffer (Cat#161-0734, manufactured by Bio-Rad Laboratories, Inc.), 1×composition: 25 mM Tris (pH 8.3), 192 mM Glycine Voltage: 200 V, electrophoresis time: 30 minutes Next, the electrophoresis gel was transferred to and stored in water, and while being irradiated with white light, the electrophoresis gel was photographed (camera: TV ZOOM-LENS 8.5-51 mm F 1.2, diaphragm: 15 to 20 (manufactured by VILBER LOURMAT), photographing machine: DP-001.FDC (manufactured by VILBER LOURMAT)). The concentration of G-CSF in a band on the gel was analyzed with image analysis software ImageJ (Ver. 1.42q) to determine the G-CSF encapsulation ratio from the following equation. The encapsulation ratio was 100%. Thus, the particle composition of the present invention is also applicable to a carrier for a protein.

G-CSF encapsulation ratio (%)=(1−amount of G-CSF in detected band/total amount of G-CSF (theoretical amount of G-CSF applied to electrophoresis gel))×100

The invention claimed is:

1. A pharmaceutical composition comprised of a drug encapsulated in a block copolymer, including a drug carrier represented by formula (1) or formula (2) as the block copolymer:

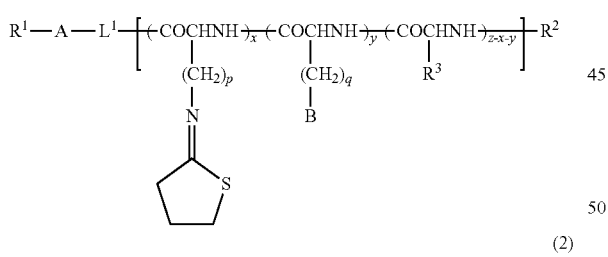

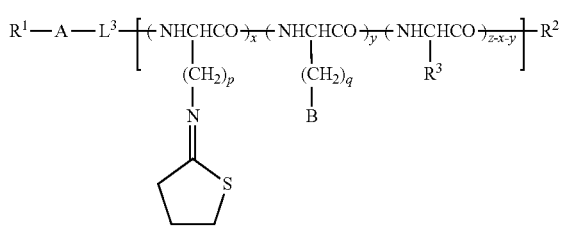

where:

R$^1$ is a hydrogen atom, a substituted or unsubstituted, linear or branched alkyl group having 1 to 12 carbon atoms or a target binding site bound to a linking group;

R$^2$ is a hydrogen atom or a substituted or unsubstituted, linear or branched alkyl group having 1 to 12 carbon atoms;

A is a hydrophilic polymer chain;

L$^1$ and L$^3$ are each a linking group;

B is a cation-containing group;

R$^3$ is a side chain of an amino acid;

z is an integer of 5 to 500;

x is an integer of 40% or more of z;

y is 0 or a positive integer;

z-x-y is 0 or a positive integer;

p is an integer of 1 to 10; and q is an integer of 1 to 10.

2. The pharmaceutical composition according to claim 1, wherein:

R$^1$ is the target binding site bound to a linking group.

3. The pharmaceutical composition according to claim 2, wherein the target binding site comprises cyclic RGD.

4. The pharmaceutical composition according to claim 1, wherein the drug comprises a biopolymer.

5. The pharmaceutical composition according to claim 1, wherein in formula (1) and formula (2), the total of said x and said y is an integer of 95% or more of said z.

6. The pharmaceutical composition according to claim 1, further comprising a target binding carrier comprising a block copolymer having a hydrophilic polymer chain, a hydrophobic polymer chain, and a target binding site bound to the hydrophilic polymer chain.

7. A method of administering a pharmaceutical composition to a patient in need thereof, comprising:

Intravenously administering to a patient a therapeutically effective amounts of the pharmaceutical composition of claim 1.

8. A pharmaceutical composition comprised of a drug encapsulated in a composition of matter having formula (1) or formula (2):

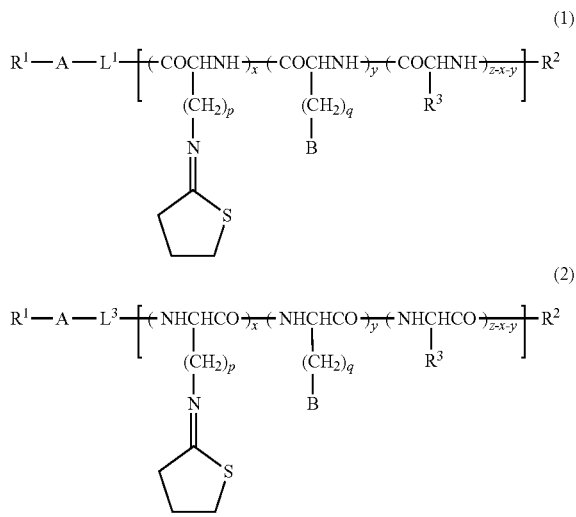

where:
R$^1$ is a hydrogen atom, a substituted or unsubstituted, linear or branched alkyl group having 1 to 12 carbon atoms or a target binding site bound to a linking group;
R$^2$ is a hydrogen atom or a substituted or unsubstituted, linear or branched alkyl group having 1 to 12 carbon atoms;
A is a hydrophilic polymer chain;
L$^1$ and L$^3$ are each a linking group;
B is a cation-containing group;
R$^3$ is a side chain of an amino acid;
z is an integer from 5 to 500;
x is an integer of 40% or more of z;
y is 0 or a positive integer;
z-x-y is 0 or a positive integer;
p is an integer from 1 to 10;
q is an integer from 1 to 10, and
when y does not equal 0 and/or when z-x-y does not equal zero, the units having a number of repetitions x, the units having a number of repetitions y and/or the units having a number of repetitions z-x-y may be arranged in any order.

9. The pharmaceutical composition according to claim 8, wherein the drug comprises a biopolymer.

10. The pharmaceutical composition according to claim 8, wherein:
A is selected from the group consisting of poly(ethylene glycol), polysaccharide, poly(vinylpyrrolidone), poly(vinyl alcohol), poly(acrylamide), poly(acrylic acid), poly(methacrylamide), poly(methacrylic acid), poly(methacrylic acid ester), poly(acrylic acid ester), polyamino acid, poly(malic acid), and derivatives thereof; and R$^3$ is a side chain of at least one amino acid selected from the group consisting of lysine, ornithine, arginine, histidine, serine, aspartic acid, and glutamic acid.

11. The pharmaceutical composition according to claim 10, wherein B is selected from the group consisting of:

—NH—(CH$_2$)$_{p3}$—[NH—(CH$_2$)$_{q3}$—]$_{r1}$NH$_2$  (i);

—NH—(CH$_2$)$_{p4}$—N[—(CH$_2$)$_{q4}$—NH$_2$]$_2$  (ii);

—NH—(CH$_2$)$_{p5}$—N{[—(CH$_2$)$_{q5}$—NH$_2$][—(CH$_2$)$_{q6}$—NH—]$_{r2}$H}  (iii); and —NH—(CH$_2$)$_{p6}$—N{—(CH$_2$)$_{q7}$—N[—(CH$_2$)$_{q8}$—NH$_2$]$_2$}$_2$  (iv)

where:
p3 to p6 and q3 to q8 are each independently 2 or 3, and r1 and r2 are each independently 1, 2 or 3.

12. The pharmaceutical composition according to claim 10, wherein:
z is an integer from 20 to 100; and
x+y is an integer that is 45% or more of z.

13. The pharmaceutical composition according to claim 12, wherein R$^1$ is the target binding site bound to a linking group and has the formula:

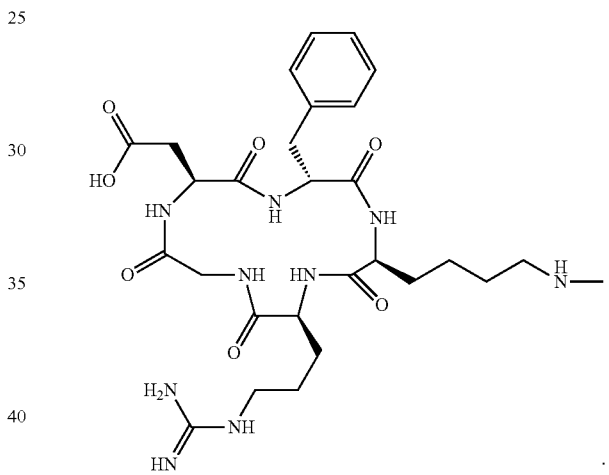

14. The pharmaceutical composition according to claim 8, wherein the drug is a nucleic acid having 18-30 bases.

15. The pharmaceutical composition according to claim 14, wherein the nucleic acid is siRNA.

16. The pharmaceutical composition according to claim 15, wherein A is poly(ethylene glycol) having 50 to 1000 ethylene glycol units, R$^3$ is the side chain of lysine, and z is 45.

17. The pharmaceutical composition according to claim 10, wherein B is —NH$^+$=C(=NH)—(CH$_2$)$_q$—SH, and q is an integer of 2 to 4.

18. A method of administering a pharmaceutical composition to a patient in need thereof, comprising:
intravenously administering to a patient a therapeutically effective amount of the pharmaceutical composition of claim 15.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: sense strand of siRNA for luciferase including
      dT terminus

<400> SEQUENCE: 1
cuuacgcuga guacuucgat t                                              21

<210> SEQ ID NO 2
<211> LENGTH: 21
<212> TYPE: DNA
<213> ORGANISM: Artificial
<220> FEATURE:
<223> OTHER INFORMATION: antisense strand of siRNA for luciferase
      including dT terminus

<400> SEQUENCE: 2
ucgaaguacu cagcguaagt t                                              21

<210> SEQ ID NO 3
<211> LENGTH: 21
<212> TYPE: DNA
<213> ORGANISM: Artificial
<220> FEATURE:
<223> OTHER INFORMATION: sense strand of non-therapeutic siRNA including
      dT terminus

<400> SEQUENCE: 3
uucuccgaac gugucacgut t                                              21

<210> SEQ ID NO 4
<211> LENGTH: 21
<212> TYPE: DNA
<213> ORGANISM: Artificial
<220> FEATURE:
<223> OTHER INFORMATION: antisense strand of non-therapeutic siRNA
      including dT terminus

<400> SEQUENCE: 4
acgugacacg uucggagaat t                                              21

<210> SEQ ID NO 5
<211> LENGTH: 21
<212> TYPE: DNA
<213> ORGANISM: Artificial
<220> FEATURE:
<223> OTHER INFORMATION: sense strand of siRNA for human vascular
      endothelial growth factor including dT terminus

<400> SEQUENCE: 5
gaucucauca ggguacucct t                                              21

<210> SEQ ID NO 6
```

```
<211> LENGTH: 21
<212> TYPE: DNA
<213> ORGANISM: Artificial
<220> FEATURE:
<223> OTHER INFORMATION: antisense strand of siRNA for human vascular
      endothelial growth factor including dT terminus

<400> SEQUENCE: 6
ggaguacccu gaugagauct t                                              21

<210> SEQ ID NO 7
<211> LENGTH: 21
<212> TYPE: DNA
<213> ORGANISM: Artificial
<220> FEATURE:
<223> OTHER INFORMATION: sense strand of siRNA for mouse vascular
      endothelial growth factor receptor including dT terminus

<400> SEQUENCE: 7
augcggcggu ggugacagut t                                              21

<210> SEQ ID NO 8
<211> LENGTH: 21
<212> TYPE: DNA
<213> ORGANISM: Artificial
<220> FEATURE:
<223> OTHER INFORMATION: antisense strand of siRNA for mouse vascular
      endothelial growth factor receptor including dT terminus

<400> SEQUENCE: 8
acugucacca ccgccgcaut t                                              21
```